(12) United States Patent
Bonmassar et al.

(10) Patent No.: US 9,579,028 B2
(45) Date of Patent: Feb. 28, 2017

(54) ARRANGEMENT AND METHOD FOR DETECTING INCONSISTENCIES AND ABNORMALITIES IN A BODY

(75) Inventors: Giorgio Bonmassar, Lexington, MA (US); John William Belliveau, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 1634 days.

(21) Appl. No.: 13/156,418

(22) Filed: Jun. 9, 2011

(65) Prior Publication Data

US 2012/0150059 A1 Jun. 14, 2012

Related U.S. Application Data

(62) Division of application No. 10/531,852, filed as application No. PCT/US03/33009 on Oct. 17, 2003, now abandoned.

(Continued)

(51) Int. Cl.
*A61B 5/02* (2006.01)
*A61B 5/0476* (2006.01)
(Continued)

(52) U.S. Cl.
CPC ........ *A61B 5/02007* (2013.01); *A61B 5/0476* (2013.01); *A61B 5/053* (2013.01); *A61B 5/055* (2013.01); *A61B 5/0536* (2013.01)

(58) Field of Classification Search
CPC ............................ A61B 5/0476; A61B 5/0482
(Continued)

(56) References Cited

U.S. PATENT DOCUMENTS 3,608,542 A 9/1971 Pacela et al.
4,314,563 A 2/1982 Wheeler
(Continued)

FOREIGN PATENT DOCUMENTS

GB 2272526 5/1994
WO 94/09699 5/1994
WO 01/08729 2/2001

OTHER PUBLICATIONS

"A comparison of the spatial sensitivity of EEG and EIT" by Ferree et al., IEEE Transactions on Medical Imaging, Feb. 15, 2001.*
(Continued)

*Primary Examiner* — Patricia Mallari
*Assistant Examiner* — Vasuda Ramachandran
(74) *Attorney, Agent, or Firm* — Quarles & Brady LLP (57) ABSTRACT

A system for detecting abnormalities or inconsistencies and a method to utilize the same are provided. In particular, a computer system may be adapted to detect the abnormality or inconsistency within at least a portion of a subject by generating internal impedance data which indicates that an impedance change within the portion of the subject has occurred. For example, the impedance change may be associated with a change in at least one characteristic of a blood vessel within the subject (such as a change in a fluid flow rate within at least a portion of the subject), a change in a fluid volume within at least a portion of the subject, etc. The impedance change also may be associated with the presence of a foreign object within the portion of the subject. In an exemplary embodiment, it is possible to detect the abnormality or inconsistency within the subject by generating a continuous, real time internal impedance map indicating the impedance change within the subject. Alternatively, the abnormality or inconsistency may be detected within the subject by generating a plurality of static internal impedance (Continued)

maps which indicate that the impedance change within the subject has occurred.

11 Claims, 7 Drawing Sheets

Related U.S. Application Data (60) Provisional application No. 60/419,256, filed on Oct. 17, 2002.

(51) Int. Cl.
*A61B 5/053* (2006.01)
*A61B 5/055* (2006.01)

(58) Field of Classification Search
USPC .................................. 600/544–545
See application file for complete search history.

(56) References Cited

U.S. PATENT DOCUMENTS

| | | | |
|---|---|---|---|
| 4,562,843 A | | 1/1986 | Djordjevich et al. |
| 4,690,149 A | | 9/1987 | Ko |
| 4,736,751 A | * | 4/1988 | Gevins et al. ............. 600/545 |
| 4,905,705 A | | 3/1990 | Kizakevich et al. |
| 5,299,569 A | * | 4/1994 | Wernicke et al. ............. 607/45 |
| 5,309,917 A | | 5/1994 | Wang et al. |
| 5,503,157 A | | 4/1996 | Sramek |
| 5,544,662 A | | 8/1996 | Saulnier et al. |
| 5,642,734 A | | 7/1997 | Ruben et al. |
| 5,919,142 A | | 7/1999 | Boone et al. |
| 6,015,393 A | | 1/2000 | Hovland et al. |
| 6,022,322 A | | 2/2000 | Prutchi |
| 6,128,518 A | | 10/2000 | Billings et al. |
| 6,201,990 B1 | | 3/2001 | Wexler et al. |
| 6,236,886 B1 | | 5/2001 | Cherepenin et al. |
| 6,330,470 B1 | * | 12/2001 | Tucker et al. ............. 600/544 |
| 6,370,424 B1 | | 4/2002 | Prutchi |
| 6,385,486 B1 | | 5/2002 | John et al. |
| 6,647,289 B2 | | 11/2003 | Prutchi |
| 6,766,191 B1 | | 7/2004 | Billings et al. |
| 2006/0122529 A1 | * | 6/2006 | Tsau ............. A61B 5/04004 600/544 |

OTHER PUBLICATIONS

"24-Bit Analog-To-Digital Converter" by Texas Instruments, Jun. 2001.*
Lionheart, W.R.B, et al. "Electrical Impedance and Diffuse Optical Tomography Reconstruction Software." Presented at the 1st World Congress on Industrial Process Tomography, Apr. 14-17, 1999. pp. 1-4.
Author Unknown. "Electrical Impedance Tomography (EIT)." Web Article. Accessed May 15, 2002. http://imasun.lbl.gov/~budinger/medTechdocs/EIT.html. pp. 1-2.
Ferree, Thomas C. et al. "A comparison of the spatial sensitivity of EEG and EIT." Preprint to be submitted to IEEE Transactions on Medical Imaging. Dated Feb. 15, 2001. http://www.csi.uoregon.edu/members/ferree/inprogress/CombinedEEGandEIT.pdf. pp. 1-16.
Boone, Kevin. "EIT: What it is, what it does." Web Article. Accessed May 15, 2002. http://www.eit.org.uk/about.html. pp. 1-2.
Rao, A. et al. Untitled Paper. Presented in the Physiological Society Meeting and the 9th International Conference on Electrical Bio-Impedance, 1995. http://www.3iwc.riken.go.jp/CONGRESS/POSTER/A10109/INT.HTM. pp. 1-5.

* cited by examiner

ARRANGEMENT AND METHOD FOR DETECTING INCONSISTENCIES AND ABNORMALITIES IN A BODY

CROSS-REFERENCE TO RELATED APPLICATIONS

This application is a divisional application of U.S. patent application Ser. No. 10/531,852, filed Sep. 26, 2005, and entitled "Arrangement And Method For Detecting Abnormalities And Inconsistencies In A Body," which claims priority to PCT No. PCT/US03/33009, filed Oct. 17, 2003, and entitled "Arrangement And Methods For Detecting Abnormalities And Inconsistencies In A Body," which claims priority to U.S. Provisional Patent Application No. 60/419,256, filed Oct. 17, 2002, and entitled "Arrangement And Method For Detecting Abnormalities And Inconsistencies In A Body," each of which are incorporated herein by reference.

FIELD OF THE INVENTION

The present invention relates generally to an arrangement and method for detecting abnormalities and inconsistencies within a subject. In particular, the present invention is directed to an arrangement and method in which a computer system detects an abnormality or inconsistency within the subject by generating internal impedance data over a predetermined range of frequencies to indicate an impedance change within the subject.

BACKGROUND OF THE INVENTION

Conventional electroencephalography (EEG) systems have been employed to record brain waves in a patient by measuring intrinsic voltages or currents produced by the brain of the patient. Specifically, conventional EEG systems detect and amplify brain waves, and convert the brain waves into digital data to be compared with data associated with normal brain waves. These systems may be employed to detect possible spinal cord injuries, stroke, epilepsy and a variety of brain dysfunctions related to a psychology of a patient ranging from substance abuse to psychosis. For example, certain conventional EEG systems include a plurality of electrodes which can be positioned on the scalp of a patient. The electrodes are coupled to a switching system, which in turn is coupled to a preamplifier that is connected to an amplifier. The amplifier is connected to a sixteen (16) bit analog to 30 digital (A/D) converter, and the A/D converter is connected to a display. The A/D converter samples the EEG waves, and converts the EEG waves into the digital data to be shown on the display. However, such conventional system only may be adapted to obtain EEG recordings.

Conventional electrical impedance tomography (EIT) systems have been employed to produce electrical impedance images in medical applications. These EIT systems measure current or voltage distributions resulting from the currents being applied to a portion of the body of the patient, and generate an image of such portion of the body based on the measured current or voltage distributions. These conventional systems have been employed, e.g., to display changes in the thorax during breathing, the stomach during a gastric emptying, the heart during intraventricular hemorrhage, and the brain due to a physiological cerebral activity, and to monitor the progression of various lung diseases. For example, the conventional EIT system can be adapted to image changes in the brain due to a physiological cerebral activity may include a current generator coupled to a switching arrangement, such as a computer controlled multiplexor. A plurality of electrodes are positioned in contact with the patient's scalp, and are coupled to the switching arrangement. An amplifier is coupled to the electrodes, a sixteen (16) bit A/D converter is connected to the amplifier, and a computer is connected to the A/D converter.

In operation, the current generator applies current to the electrodes. For example, the current may be applied sequentially to the electrode pairs, or simultaneously to multiple pairs of electrodes, which is known as a parallel data collection. Moreover, potential differences between the electrode pairs may be measured to obtain analog signals, and these analog signals may be amplified by the amplifier. Subsequently, the A/D converter converts the analog signals to digital signals, and forwards the digital signals to the computer. In this manner, the data may be processed by the reconstruction software to obtain image changes in the brain due to a physiological cerebral activity, and provide these images on a display. However, such conventional system may be adapted to only obtain EIT recordings that are e.g., associated with the physiological cerebral activity, and may also be adapted to only monitor only certain organs. Moreover, such convention system only may obtain EIT recordings at a particular frequency.

SUMMARY OF THE INVENTION

Therefore, a need has arisen to provide an arrangement and method for detecting abnormalities and inconsistencies which overcome the above-described and other shortcomings of the related art.

One of the advantages of the present invention is that the arrangement and method are provided which may detect the abnormality or inconsistency within a subject by generating internal impedance data that indicates the occurrence and/or particulars of an impedance change within the associate subject has for at least one characteristic of a blood vessel within the subject. For example, the impedance change associated with the change in the characteristic of the blood vessel may be a change of a fluid flow rate within at least a portion of the subject, a change of a fluid volume within at least a portion of the subject, etc. Another advantage of the system and method of the present invention is that the abnormality or inconsistency within a subject may be detected by generating internal impedance data that indicates an impedance change within the subject associated that is with the presence of a foreign object within at least a portion of the subject. Yet another advantage of the system and method of the present invention is that they allow simultaneous spectral electrical impedance tomoD-aphy (SEIT) recordings and electroencephalography recordings, and/or simultaneous spectral electrical impedance tomography recordings and current density recordings to be obtained from the subject. Still another advantage of the present invention is that the system may be a portable system, so that it may be used by first responders to accidents, e.g., Emergency Medical Service (EMS) personnel, in order to assist the responders in obtaining data which is useful in making decisions concerning abnormalities or inconsistencies, such as injuries to the brain or torso involving foreign objects and/or internal bleeding.

According to an exemplary embodiment of the present invention, an arrangement and method utilize a computer system which may be adapted to detect abnormalities and inconsistencies within a subject, e.g., a human or an animal, by generating internal impedance data which indicates the occurrence and/or the particulars of an impedance change within at least a portion (e.g., a brain or a torso) of the subject has occurred. For example, the impedance change may be associated with a change in at least one characteristic of a blood vessel within the subject, such as a change in a fluid (e.g., blood, flow rate within at least a portion of the subject) a change in a fluid volume within at least a portion of the subject, etc. The impedance change may also be associated with the presence of a foreign object (e.g., a metal foreign object) within at least a portion of the subject. Moreover, the internal impedance data may be obtained over a predetermined range of frequencies, such as between about 0.01 Hz and about 100 KHz. As examples the Cole-Cole or 4-Cole-Cole models may be used to determine tissue's impedance at a given frequency. In another exemplary embodiment of the present invention, the computer system may adapted to detect the abnormality or inconsistency within the subject by generating a continuous, real time internal impedance map which indicates the occurrence and/or the particulars of the impedance change within the portion of the subject. Alternatively, the computer system may be adapted to detect the abnormality or inconsistency within the subject by generating a plurality of static internal impedance maps which also may indicate the occurrence and/or the particulars of the impedance change within the subject.

In yet another exemplary embodiment of the present invention, it is possible to utilize an electrical stimulator, a switch coupled to the electrical stimulator, and a plurality of electrodes positioned on at least a portion of the subject and coupled to the switch. An analog to digital (A/D) converter can also be provided such that it is coupled to the switch and to each of the electrodes. Moreover, the computer system may be coupled to the switch and to the AJD converter. In operation, the electrical stimulator may apply current to at least a pair of the electrodes, and the A/D converter may measure voltage or current distributions resulting from the applied current. The applied current may be white noise or pink noise, depending on whether SEIT are being recorded, or whether SEIT and EEG signals are being simultaneously recorded. The A/D converter may also transmit the voltage or current distributions to the computer system so that the computer system may generate the internal impedance data based on the voltage or current distributions.

As examples, the computer system may use the Barber-Brown linear backprojection method, the Calderon approach, the moment method, the one-step Newton method, the least squares method, or constrain minimixation methods in combination with an approximation model of the at least one portion of the subject (e.g. the head of the subject) to generate the internal impedance maps. Specifically, a map of the current flow through the head may be generated using the Barber-Brown backprojection method. Moreover, the computer system may include a database of approximated head models, and each approximation head model may be based on predetermined characteristics associated with an imaginary subject, such as a predetermined height, age, sex, etc., of the imaginary subject. Each approximation head model may indicate an expected current flow through the head of a subject who's characteristics are the same as or are similar to the predetermined characteristics. The computer system may select an appropriate approximated head model for the subject based on the characteristics of the subject, and the computer system then may alter the current flow map obtained using the Barber-Brown linear backprojection method based on the selected approximation head model to obtain the internal impedance maps.

According to still yet another exemplary embodiment of the present invention the A/D converter is, e.g., a twenty-four (24) bit, thirty-two (32) channel A/D converter, adapted to obtain simultaneous spectral electrical impedance tomography recordings and electroencephalography recordings from the subject. In a variation of this embodiment, the electrical stimulator and the computer system can be positioned externally from a magnetic resolution environment, such that the twenty-four (24) bit, thirty-two (32) channel A/D converter may be adapted to obtain simultaneous spectral electrical impedance tomography recordings and current density recordings from the subject.

BRIEF DESCRIPTION OF THE DRAWINGS

For a more complete understanding of the present invention, the needs satisfied thereby, and the objects, features, and advantages thereof, reference now is made to the following descriptions taken in connection with the accompanying drawings.

FIG. 3b is a flow diagram depicting a variation of the method of FIG. 3a.

FIG. 4b is a flow diagram depicting a first variation of the method of FIG. 4a.

FIG. 4c is a flow diagram depicting a second variation of the method of FIG. 4a.

DETAILED DESCRIPTION OF THE PREFERRED EMBODIMENTS

Exemplary embodiments of the present invention and their advantages may be understood by referring to FIGS. 1-4c, like numerals being used for like corresponding parts in the various drawings.

Figure 1:
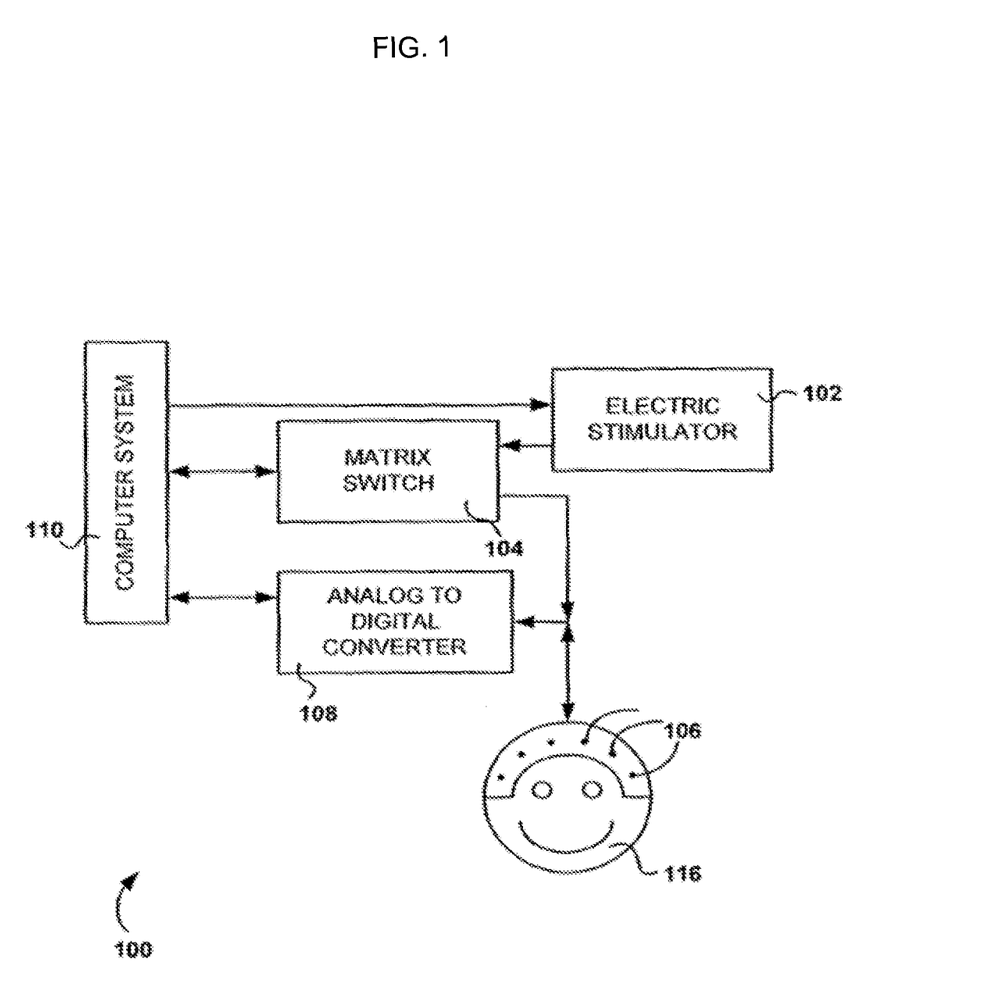
FIG. 1 is a schematic diagram of a first exemplary embodiment of an arrangement according to a first embodiment of the present invention for detecting abnormalities and inconsistencies in a subject.

Referring to FIG. 1, a first exemplary embodiment of an arrangement 100 according to the present invention for detecting abnormalities and inconsistencies in a subject is provided. The arrangement 100 may include a computer system 110 which can be adapted to detect an abnormality or inconsistency within at least a portion of a subject 116. Specifically, the computer system 110 may detect the abnormality or biological inconsistency by generating internal impedance data. For example, the computer system 110 may generate the internal impedance data over a predetermined range of frequencies, such as between about 0.01 Hz and about 100 KHz. This internal data indicates the occurrence and/or the particulars of an impedance change within the subject 116 (associated with a change in at least one characteristic of a blood vessel within the subject). Alternatively, the internal impedance data may be associated with a presence of a foreign object within at least a portion of the subject 116.

In an exemplary embodiment of the present invention, the impedance change associated with the change in the at least one characteristic of the blood vessel may be a variance in a fluid flow rate (e.g., a blood flow rate) within at least a portion of the subject 116. Alternatively, the impedance change can be 'a change in a fluid volume (e.g., a blood volume) within at least a portion of the subject. In another exemplary embodiment of the present invention, the subject 116 may be a human being, an animal, etc., and the arrangement 100 may be adapted to detect the abnormality within a brain, a torso, etc. of the subject 116. Moreover, the abnormalities or biological inconsistencies may include an injury (such an injury associated with internal bleeding), the presence of a foreign object within the subject 116, or any other internal or external abnormality or biological inconsistency resulting in a change in impedance within the subject 116. In these exemplary embodiments of the present invention, the impedance of blood is generally smaller than the impedance of a brain tissue (i.e., the conductivity of the blood is greater than the conductivity of the brain tissue), and is also less than the impedance of a tissue in the torso and other parts of the subject 116. When the blood volume or the blood flow in the brain, the torso, or any other part of the subject 116 increases (such as when a blood vessel is believed to be likely punctured or expanded), the impedance of at least a portion of the subject 116 decreases. For example, when the blood vessel is punctured, the blood flows from the punctured blood vessel, and the impedance of the tissue adjacent to the punctured blood vessel may decrease. Similarly, when the blood volume or the blood flow in the brain, the torso, or any other part of the subject 116 decreases (such as when a blood vessel is constricted), the impedance of at least a portion of the subject 116 may increase. Moreover, the impedance of a foreign object (e.g., a metal foreign object, such as a bullet, shrapnel, etc.) may be smaller than the impedance of the brain tissue, and can also be smaller than the impedance of the tissue in the torso or other parts of the subject 116. As such, when a foreign object is present in the brain, torso, or any other part of the subject 116, the impedance of at least a portion of the subject 116 is decreased. As such, the arrangement 100 may be employed to determine whether the abnormality or biological inconsistency may exist (e.g., an injury to or the presence of a foreign object within the subject 116) by generating data associated with these changes in the impedance.

In particular, an exemplary embodiment of the arrangement 100 of the present invention may also include a plurality of electrodes 106 positioned on at least a portion of the subject 116, an electrical stimulator 102 (e.g., a function generator, such as a current function generator or a voltage function generator), a matrix switch 104 (e.g., a thirty-two (32) channel, analog matrix switch), and an A/D converter 108 (e.g., a thirty-two (32) channel, twenty-four (24) bit A/D converter). The electrical stimulator 102 may be coupled to the matrix switch 104, and the matrix switch 104 may be coupled to the electrodes 106 and the computer system 110. Moreover, the electrodes 106 may be coupled to the A/D converter 108, which can be coupled to the computer system 110, and the computer system 110 may be coupled to the electrical stimulator 102. For example, the matrix switch 104 may be connected to the computer system 110 using an optical digital link, and the A/D converter 108 can be connected to the computer system 110 using an optical USB link. In this configuration, the computer system 110 may be used to control each component of the arrangement 100.

In operation, the electrical stimulator 102 can apply a current or a voltage to at least one pair (e.g., may simultaneously apply a current or a voltage to eight (8) pairs) of the electrodes 106, and the A/D converter 108 can continuously measure the voltage and/or current distributions at the electrodes 106 to which the current is not being applied. The applied current may be white noise or pink noise. For example, when the A/D converter 108 is obtaining SEIT recordings from the subject 112, the applied current may be white noise. Specifically, the frequency range of white noise may not overlap with the frequency range at which SEIT signals are detected (e.g., between about 50 Hz and about 100 KHz). Consequently, the white noise may not interfere with the recordation of SEIT signals. However, when the A/D 30 converter 108 is simultaneously obtaining EEG recordings and SEIT recordings from the subject 112, the applied current may be pink noise. Specifically, the frequency range of pink noise may not overlap with the frequency range at which EEG signals are detected (e.g., between about 0.01 Hz and about 50 Hz). Consequently, the pink noise may not may not interfere with the recordation of EEG signals. If the pink noise does interfere with the recordation of EEG signals, the unwanted pink noise readily may be filtered out (e.g, using an adaptive filter). Moreover, although the frequency range of pink noise may overlap with the frequency range at which SEIT signals are detected, the effect of such pink noise on the SEIT signals may be minimal.

In any of the above-described exemplary embodiments of the present invention, after electrical stimulator 102 applies the current or the voltage to the at least one pair of the electrodes 106, and the AM converter 108 measures the voltage and/or current distributions at the electrodes 106 to which the current or voltage is not being applied, the matrix switch 104 switches the current to another one or more parts of the electrodes 106, and the A/D converter 108 obtains additional voltage or current distribution measurements from those electrodes. Thereafter, the A/D converter 108 converts the analog voltages into digital data, and forwards the converted digital data to the computer system 110.

When the computer system 110 receives the digital data from the A/D converter 108, the computer system 110 can generate the internal impedance data which indicates the occurrence and/or the particulars of the impedance change within the subject 116. The impedance change is associated with a change in at least one characteristic of a blood vessel within the subject and/or with a presence of a foreign object within at least a portion of the subject 116. For example, the computer system 110 may generate a continuous, real time internal impedance map indicating the impedance change within the subject 116. Alternatively, the computer system 110 may generate a plurality of static internal impedance maps indicating the impedance change within the subject 116. In addition, the computer system 110 may be adapted to compensate for impedance variations resulting from the attachment of the at least one electrode 106 to the subject 116 (e.g., variations resulting from the use of paste to attached the at least one electrode to the subject 116, cleansing of the portion of the subject 116 which the at least one electrode is attached, etc.). For example, the computer system 110 may compensate for the impedance variations resulting from the attachment of the at least one electrode 106 to the subject 116 by usMg frequency spectrum normalizations.

In an exemplary embodiment of the present invention, the computer system 110 may generate the internal impedance maps by using a known linear approximation method, such as the Barber-Brown linear backprojection method, Calderon's method, a moment method, or a one-step Newton method. Each of these linear approximation methods readily will be understood by those of ordinary skill in the art. In another exemplary embodiment of the present invention, the computer system 110 may generate the internal impedance maps by using a known iterative method, such as by employing a layer-stripping algorithm.

Alternatively, the computer system 110 may use the Barber-Brown linear backprojection method in combination with an approximation model of the at least one portion of the subject 116 (e.g., the head of the subject 116) to generate the internal impedance maps. For example, in accordance with the Barber-Brown linear backprojection method, a pair of detectors (not shown) may be positioned on opposite sides of the head and may obit the head. As the detectors orbit the head, two twin particles may be continuously transmitted to the detectors, and a map of the current flow through the head may be generated. However, as the frequency of the current flowing through the head decreases, the difficulty of obtaining data sufficient to generate an accurate map of the current flow through the head increases. Consequently, at least certain frequencies, using the Barber-Brown linear backprojection method by itself may not be sufficient to generate an accurate map of the current flow through the head. In this exemplary embodiment of the present invention, the approximation model of the head may be used in combination with the above-described current data obtained using the Barber-Brown linear backprojection method to generate the internal impedance maps. Specifically, the computer system 110 may include a database of approximated head models, and each approximation head model may be based on predetermined characteristics associated with an imaginary subject, such as a predetermined height, age, sex, etc., of the imaginary subject. Moreover, each approximation head model may indicate an expected current flow through the head of a subject 116 who's characteristics are the same as or are similar to the predetermined characteristics. The computer system 110 may select an appropriate approximated head model for the subject 116 based on the characteristics of the subject 116, and the computer system 110 then may alter the current flow map obtained using the Barber-Brown linear backprojection method based on the selected approximation head model to obtain the internal impedance maps.

In another variation of the present invention, the arrangement 100 may be a portable abnormality detection arrangement. As such, the arrangement 100 may be used by first responders to accidents (e.g., EMS personnel) in order to assist the responder in obtaining data that is useful in making decisions concerning abnormalities or biological inconsistencies, such as injuries to the brain or torso involving foreign objects and/or internal bleeding. Further, in yet another variation of the arrangement 100, the A/D converter 108 can be a thirty-two (32) channel, twenty-four (24) bit A/D converter, and thus the bandwidth of the arrangement 100 may be sufficient to allow the computer system 110 to obtain simultaneous SEIT and EEG recordings. These simultaneous SEIT and EEG recordings allow the computer system 110 to gather information related to different types of medical problems, simultaneously. For example, the SEIT recordings may be used to detect the presence of the foreign object in the subject 116, and can detect an increase in the blood to the brain, torso, or any other body part due to trauma. In contrast, the EEG recordings may be used to detect strokes, epilepsy, spinal cord injuries, substance abuse, and any other injury or occurrence which can affect the brain to emit the corresponding waves.

Figure 2:
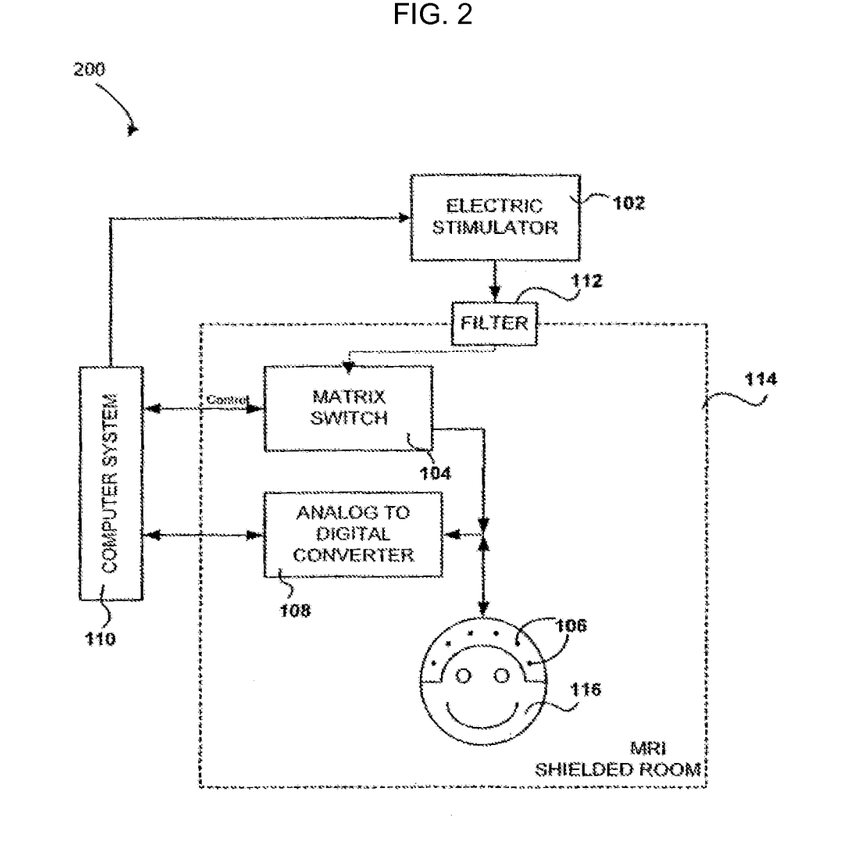
FIG. 2 is a schematic diagram of a second-exemplary embodiment of the arrangement of the present invention.

FIG. 2 shows a second exemplary embodiment of the arrangement 200 for detecting the abnormalities or biological inconsistencies for use within a magnetic resonance imaging (MIRI) environment 114 according to the present invention. The features and advantages of the second embodiment of the arrangement 200 of the present invention are substantially similar to the features and advantages of the second embodiment of the present invention, except as provided herein below. In the second exemplary embodiment of the arrangement 200 of the present invention, the electrical stimulator 102 and the computer system 110 may be positioned externally from the MRI environment 114, and the arrangement 200 may further include at least one filter 112 (e.g., at least one radio frequency filter) communicatively connected between the electrical stimulator 102 and the matrix switch 104. Moreover, the filter 112 may be adapted to filter the current applied by the electrical stimulator 102 before the current is transmitted into the MRI environment 114.

In this exemplary embodiment of the present invention, the A/D converter 108 may be adapted to obtain simultaneous SEIT recordings and current density recordings from the subject 116. Specifically, imaging techniques such as a current density imaging ("CDI") technique can be utilized to generate electrical current density distributions in a volume of the subject 116 being examined using the MIRI techniques. For example, when the electrical stimulator 102 applies the electrical current to the subject 116, the computer system 110 may receive MRI data and SEIT data from the A/D converter 108. Using known mathematical techniques, the computer system 110 can process the MRI data so as to convert the MRI data into current density distribution data, which may be used to determine a current flow or a current path within the subject 116. After the current flow within the subject 116 is determined, the location of particular portions of the subject 116 in which an impedance change or impedance spike occurs may be determined more precisely. Consequently, an internal impedance map, generated by the computer system 110 based on the SEIT data and the current density distribution data, may have a greater spatial resolution than an internal impedance map which is generated based on the SEIT data.

Figure 3A:
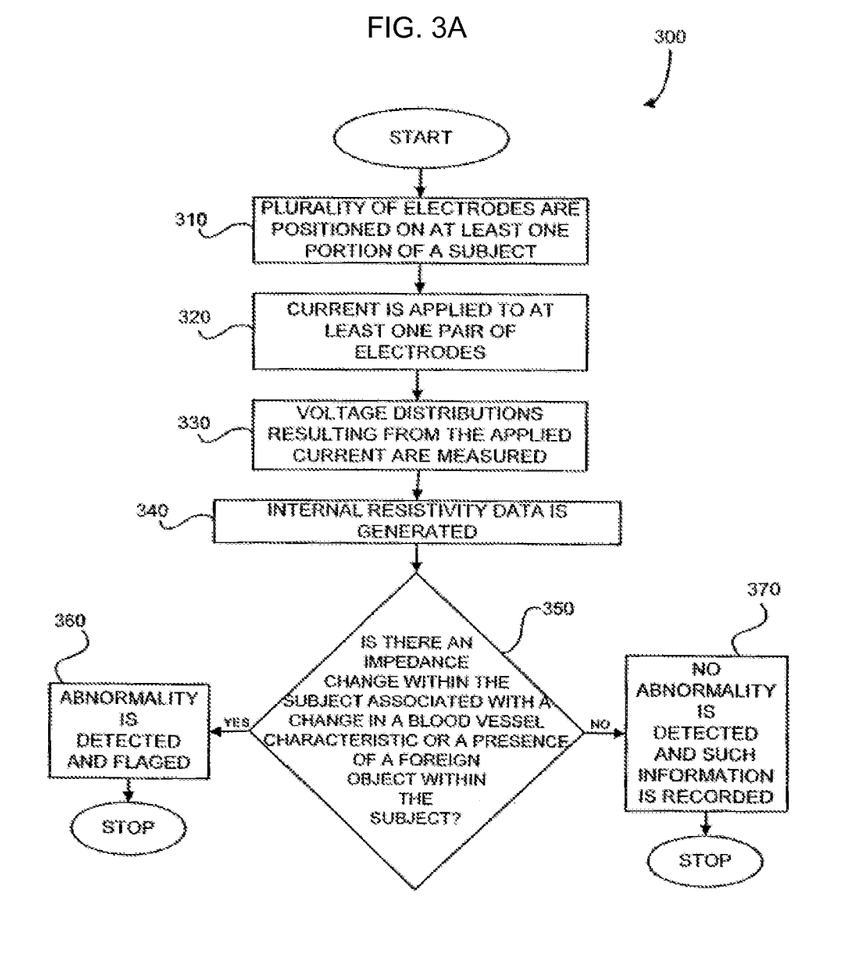
FIG. 3a is a flow diagram of a first exemplary embodiment of a method according to the present invention for detecting abnormalities and inconsistencies 10 within the subject.
Figure 3B:
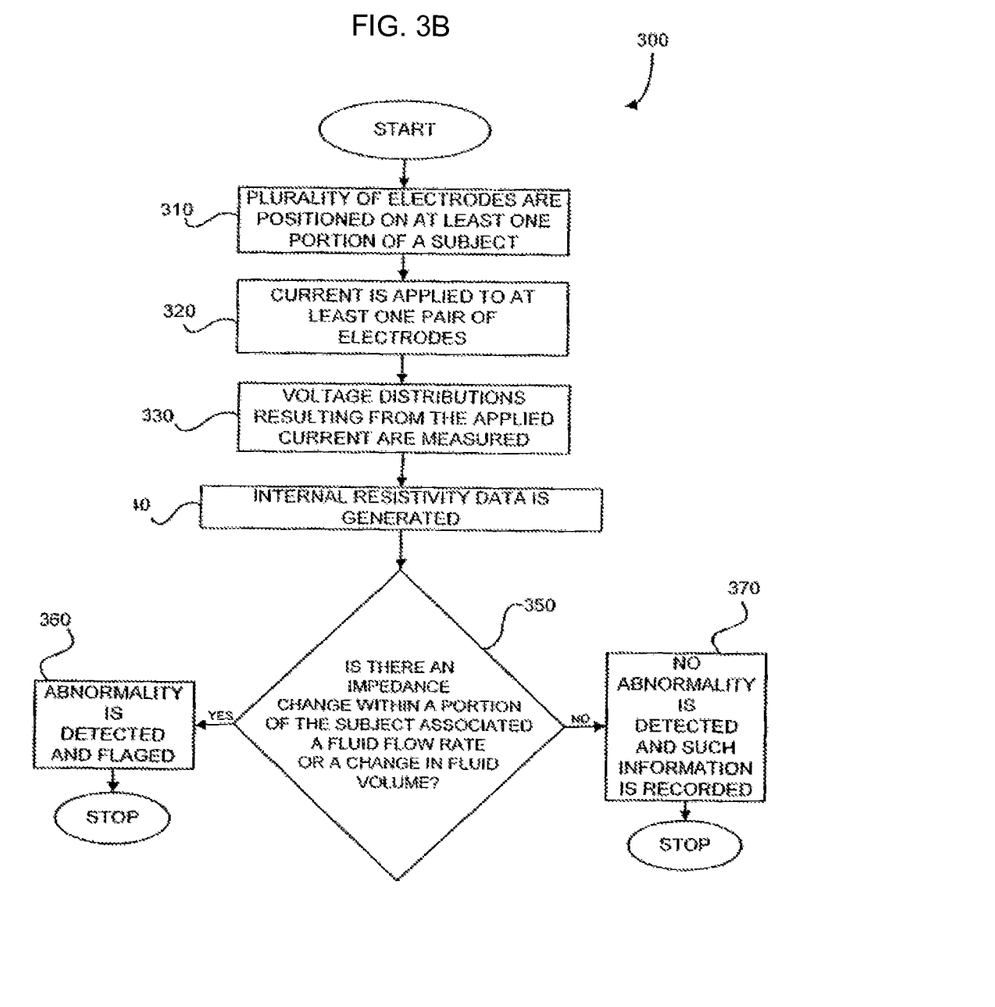

Referring to FIG. 3a, a flow diagram of a first exemplary embodiment of a method 300 which can be used by the arrangement 100 of FIG. 1 is depicted. In step 310, a plurality of electrodes 106 may be positioned on at least a portion of the subject 116. In step 320, a current can be applied to at least one pair of the electrodes 106 (or even to a single electrode). In step 330, voltage or current distributions resulting from the applied current may be measured. Then, in step 340, the internal impedance data is generated. A user of the arrangement 100 determines whether the internal impedance data indicates an impedance change within the subject 116 in step 350. This impedance change is associated with a change in the blood vessel characteristic and/or a presence of the foreign object within at least a portion of the subject 116. Referring to FIG. 3b, in a variation of the first exemplary embodiment of the method 300 according to the present invention, step 350 may be replaced by step 350'. In step 350', the user of the arrangement 100 determines whether the internal impedance data indicates the impedance change within subject 116 that is associated with a change in fluid flow rate (e.g., a blood flow rate) and/or the change in fluid volume (e.g., a blood volume) within the subject 116. In either one of the variants of the method 300 illustrated in FIGS. 3a and 3b, if the internal impedance data indicates such impedance change, in step 360, the user of the arrangement 100 detects an abnormality within the subject 116. If the internal impedance data does not indicate such an impedance change, in step 370, the user of the arrangement 100 detects the absence of an abnormality or biological inconsistency within the subject 116.

Figure 4A:
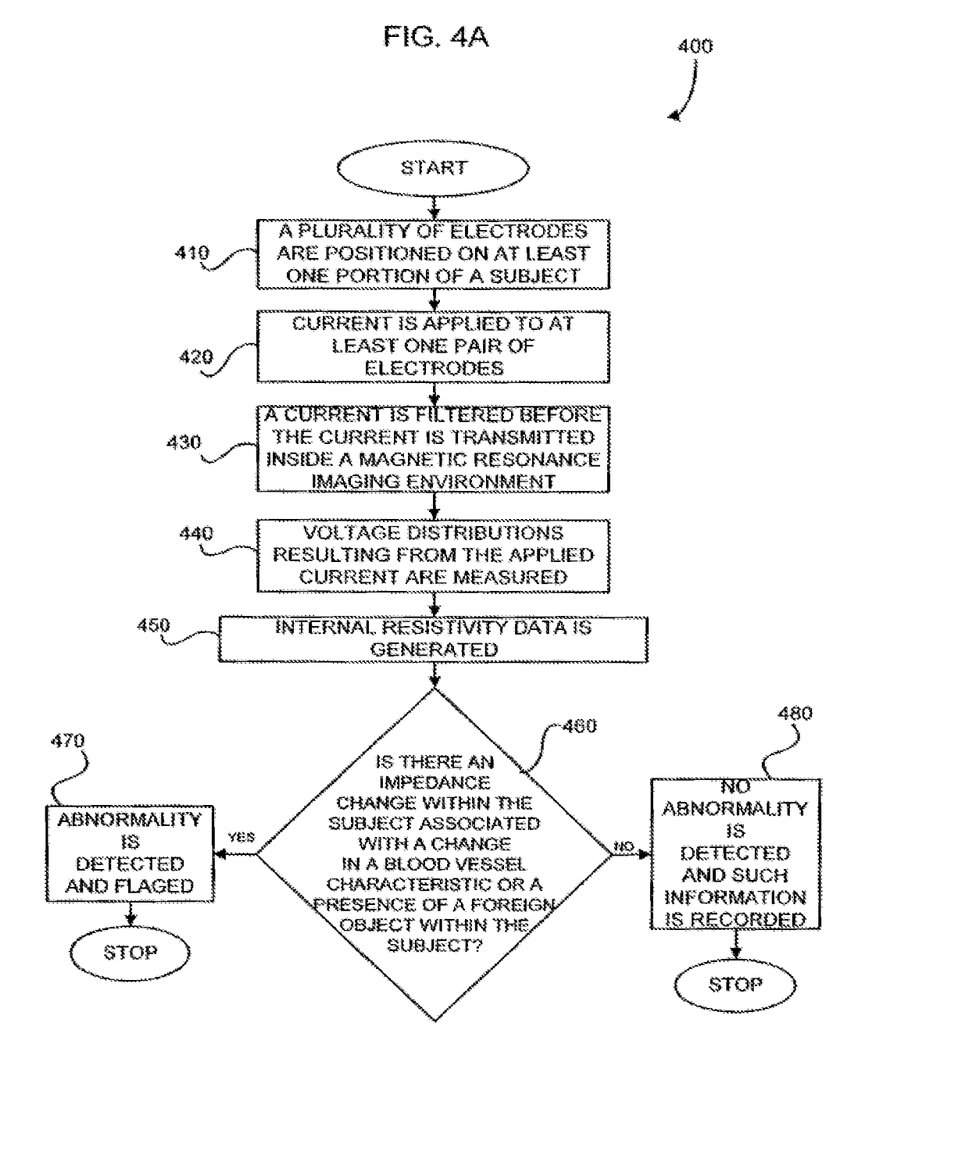
FIG. 4a is a flow diagram of a second exemplary embodiment of the method according to the present invention.
Figure 4B:
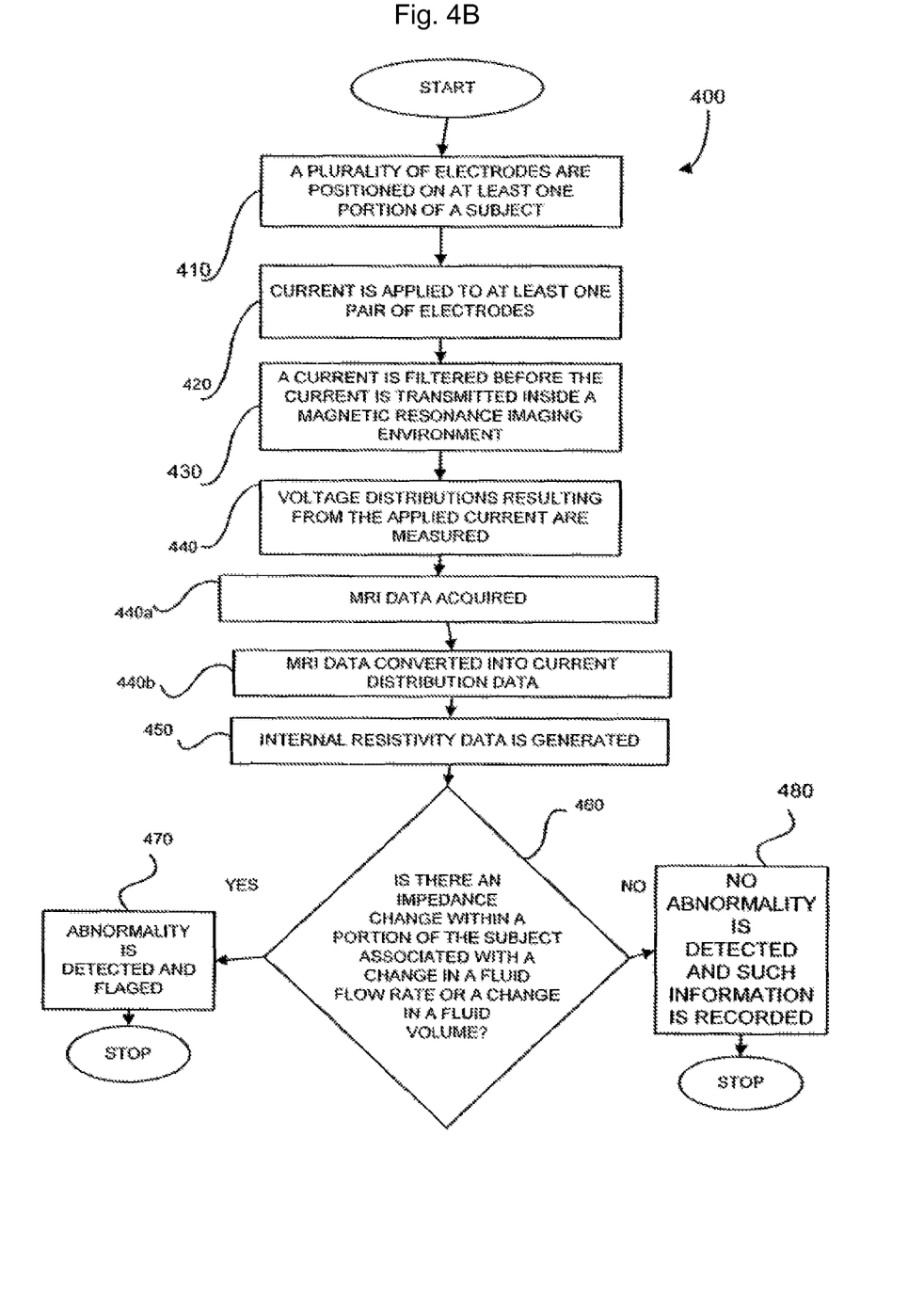
Figure 4C:
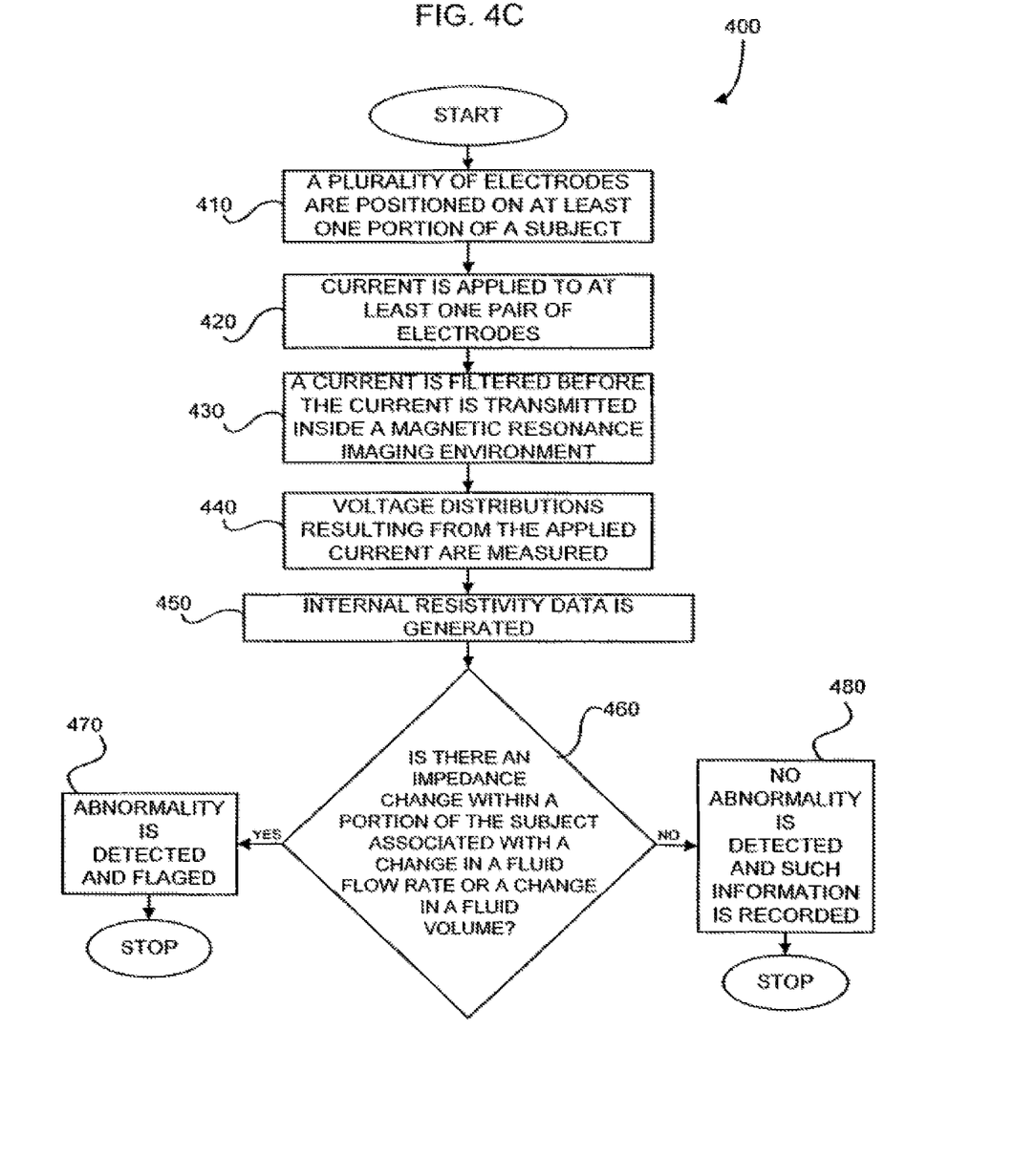

Referring to FIG. 4a, a flow diagram of a second embodiment of a method 400 according to the present invention which is used by the arrangement 200 of FIG. 2 is depicted. In step 410, the electrodes 106 may be positioned on at least a portion of the subject 116. In step 420, the current can be applied to at least a pair of the electrodes 106. Further, in step 430, the current may be filtered before the current is transmitted inside the MR1 environment. In step 440, the voltage or current distributions resulting from the applied current may be measured. Referring to FIG. 4b which shows a first variation of the second exemplary embodiment of the method 400 according to the present invention, this method is substantially the same as that of FIG. 4a, except steps 440a and 440b can also be provided. In step 440a, MRI data may be acquired, and in step 440b, the MR1 data may be converted into voltage or current distribution data. Moreover, in step 450, the internal impedance data is generated. For example, the internal impedance data can be based on the voltage or current distributions. In step 460, the user of the arrangement 200 determines whether the internal impedance data indicates the impedance change within the subject 116 associated with a change in a blood vessel characteristic, and/or a presence of the foreign object within at least a portion of the subject 116. Referring to FIG. 4c, in a second variation of the second exemplary embodiment of the method 300 of the present invention, step 460 may be replaced by step 460'. In step 460', the user of the arrangement 200 determines whether the internal impedance data indicates the impedance change within subject 116 associated with the change in fluid flow rate (e.g., the blood flow rate) and/or a change in fluid volume (e.g., the blood volume) within the subject 116. In either of the flow diagrams of FIGS. 4a and 4b, if the internal impedance data indicates such impedance change, in step 470, the user of the arrangement 200 detects an abnormality within the subject 116. If the internal impedance data does not indicate such impedance change, in step 480, the user of the arrangement 200 detects the absence of the abnormality or biological inconsistency within the subject 116.

While the invention has been described in connection with preferred embodiments, it will be understood by those of ordinary skill in the art that other variations and modifications of the preferred embodiments described above may be made without departing from the scope of the invention. Other embodiments will be apparent to those of ordinary skill in the art from a consideration of the specification or practice of the invention disclosed herein. It is intended that the specification and the described examples are considered as exemplary only, with the true scope and spirit of the invention indicated by the following claims.

What is claimed is:

1. A system for the detection of stroke in a subject, the system comprising:
   an electrical stimulator configured to apply a current comprised of pink noise to at least one pair of electrodes, the electrodes configured to be positioned on a skull of the subject to apply the current and to receive brain activity of the subject;
   an analog to digital (A/D) converter configured to record the brain activity of the subject in the form of spectral electrical impedance tomography recordings and electroencephalography recordings, simultaneously; and
   a computer system configured to generate real time spectral electrical impedance data from the spectral electrical impedance tomography recordings, the spectral electrical impedance data indicating an impedance change within the brain of the subject, wherein the impedance change is associated with an indication of stroke.

2. The system of claim 1, wherein the electroencephalography recordings are used to provide an indication of an occurrence that affects the brain.

3. The system of claim 2, wherein the occurrence that affects the brain includes at least one of stroke, epilepsy, spinal cord injury, and substance abuse.

4. The system of claim 1, wherein the impedance change associated with the indication of stroke is at least one of: a change in a fluid flow rate within the brain of the subject, and a change in a fluid volume within the brain of the subject.

5. The system of claim 4, wherein the fluid includes blood.

6. The system of claim 1, wherein the computer system generated real time spectral electrical impedance data comprises a real time spectral electrical impedance map to detect the indication of stroke within the subject.

7. The system of claim 1, wherein the computer system generates a plurality of static spectral electrical impedance maps to detect the indication of stroke.

8. The system of claim 1, wherein the electrical stimulator is a function generator.

9. The system of claim 1, wherein the A/D converter is a thirty-two channel, twenty-four bit A/D converter.

10. A system for the detection of stroke in a subject, the system comprising:
    an electrical stimulator configured to apply a current comprised of pink noise to at least one pair of electrodes, the electrodes configured to be positioned on a skull of the subject to apply the current and to receive brain activity of the subject;
    an analog to digital (A/D) converter configured to record the brain activity of the subject in the form of spectral electrical impedance tomography recordings and electroencephalography recordings, simultaneously; and
    a computer system configured to generate real time spectral electrical impedance data from the spectral electrical impedance tomography recordings, the spectral electrical impedance data indicating an impedance change within the brain of the subject, wherein at least one of the impedance change and the electroencephalography recordings provides an indication of stroke.

11. The system of claim 1, wherein the computer system is further configured to generate real time electroencephalography data from the electroencephalography recordings, and the real time spectral electrical impedance data and the electroencephalography data are each transformed into representations of different types of medical problems simultaneously, and the representations are used together to make decisions concerning abnormalities or biological inconsistencies.

* * * * *